July 8, 1969 R. G. JELLY Plant Pat. 2,902
ROSE PLANT
Filed Dec. 18, 1967
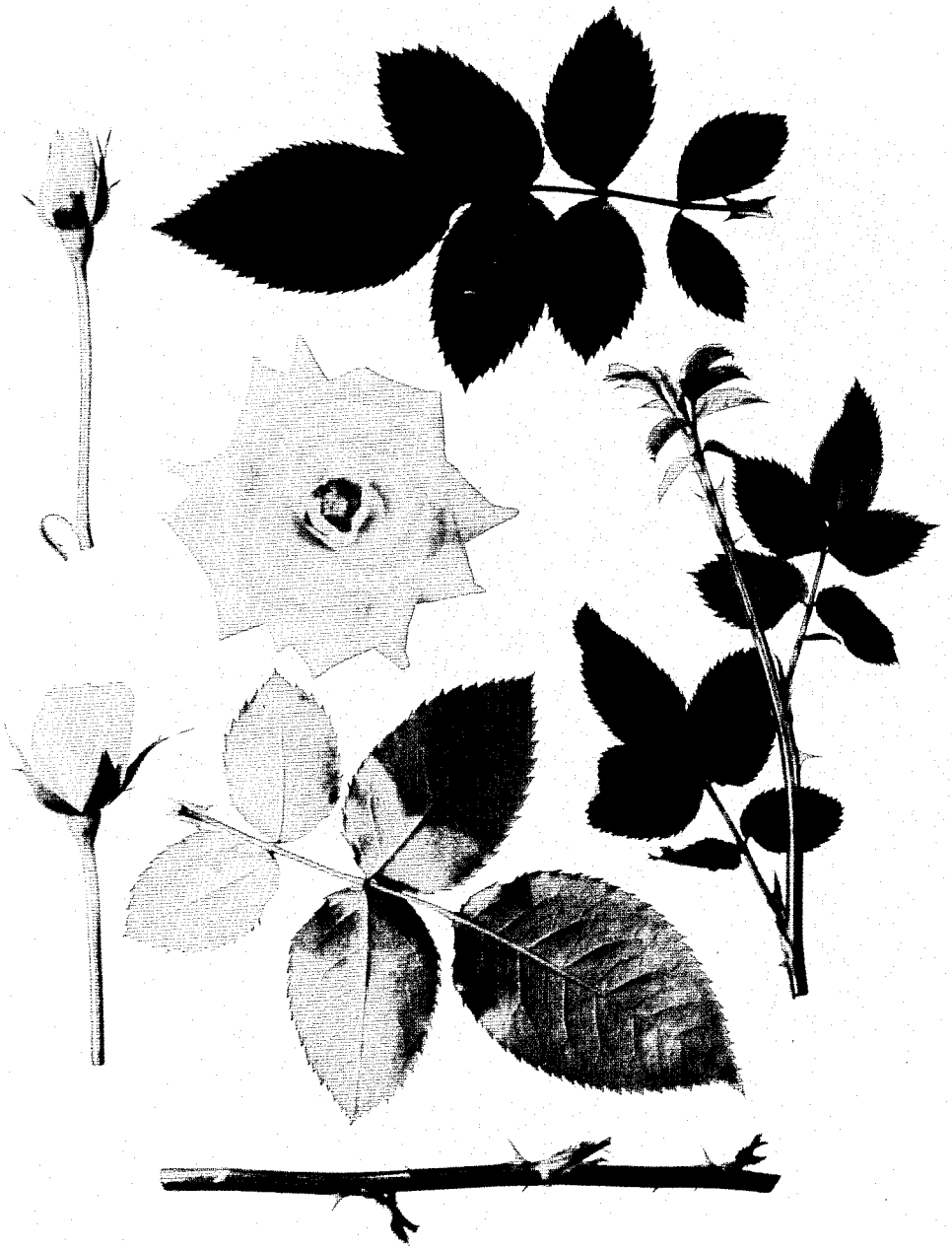
Inventor.
Robert G. Jelly
By: Robb & Robb
Attorneys.

United States Patent Office

Plant Pat. 2,902
Patented July 8, 1969

2,902
ROSE PLANT

Robert G. Jelly, Richmond, Ind., assignor to E. G. Hill Co., Inc., Richmond, Ind., a corporation of Indiana Filed Dec. 18, 1967, Ser. No. 691,664
Int. Cl. A01h 5/02
U.S. Cl. Plt.—22 1 Claim The present invention relates to a new and distinct variety of rose plant of the floribunda class, which was originated by me by crossing an unnamed and unpatented orange flower colored seedling identified in my breeding records as #47–58–O.S. with another unnamed and unpatented orange flower colored seedling identified as #7–59–O.S., the former being the seed parent and the latter being the pollen parent.

In the past, floribunda rose varieties of orange flower colors have either been deficient in flower productivity or deficient in flower lasting quality as cut flowers. Accordingly, the primary objective of the breeding of my new variety was to produce an improved floribunda variety having long-lasting flower qualities, along with a basic orange flower color satisfying the desires of consumers in this color range. This objective was fully achieved, along with other desirable improvements, as evidenced by the following unique combination of characteristics which are outstanding in the new variety and which distinguish it from its parents, as well as from all other rose varieties of which I am aware:

(1) An upright habit of growth;
(2) Uniformity of cane size;
(3) Excellent flower productivity when grown under glass;
(4) A distinctive and attractive salmon-orange flower color; and
(5) Excellent keeping qualities of the flowers as cut flowers.

In comparison with its unnamed seed parent, the new variety has a better growing habit; the flower stems have a more desirable length suitable for cut flowers; a brighter flower color; and excellent keeping qualities.

As compared with its unnamed pollen parent, the new variety has a better and somewhat shorter flower stem length which is more normal in proportion to the bud size, contrary to the stem length of the parent variety which is too long for the bud size.

Asexual reproduction of the new variety by grafting, as performed by me at Richmond, Ind., and also by budding, as performed at Livermore, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert S. Wilson's Horticultural Colour Chart (hereinafter abbreviated as (W)), Koster's Color Guide (hereinafter abbreviated as (K)), and Nickerson Color Fan (hereinafter abbreviated as (N)), as indicated, except where general color terms of ordinary dictionary significance are obvious:

Type: Seedling; greenhouse; for cut flowers.
Class: Floribunda.
Breeding: Seedling.
*Seed parent.*—As unnamed and unpatented orange flowered seedling #47–58–O.S.
*Pollen parent.*—An unnamed and unpatented orange flowered seedling #7–59–O.S.

Propagation: Holds its distinguishing characteristics through succeeding propagations by both grafting and budding.

*Flower*

Locality where grown and where following observations were made: Richmond, Ind.
Flowers borne: Usually from one to three to a stem, but can be disbudded singly for commercial purposes; in an irregular cluster; on moderate strong stems, of medium length.
Quantity of bloom: Free, in greenhouse.
Continuity: Continuous, in greenhouse.
Fragrance: Moderate, in greenhouse. Nature—spice.
Bud:
*Peduncle.*—Medium length; from small to medium diameter; erect. Bark—almost smooth. Color—Fern Green, Plate 0862 (W). Thorns—non. Prickles—none. Hairs—none.
*Before calyx breaks.*—Size—small. Form—short pointed; with a conspicuous neck; with foliaceous appendages on the surface of the bud; with slender foliaceous parts extending beyond the tip of the bud equal to ¾ or more of its length. Color—Moderate Yellow Green 5GY 5/6 (N).
*As calyx breaks.*—Outside color—slightly lighter than Mandarin Red, Plate 17/1 (W).
*As first petal opens.*—Size—small. Form—short-pointed. Color: outside—slightly lighter than Mandarin Red, Plate 17/1 (W); inside—Mandarin Red, Plate 17 (W).
*Opening.*—Opens up well in greenhouse; is affected by extremely hot, dry weather by a slight reduction in flower size.
Bloom:
*Size (when fully open).*—Small; from 3 inches to 3½ inches.
*Petalage.*—Double; from 24 to 35 petals; arranged regularly.
*Form.*—High-centered at first but becoming fairly flat; petals being at first rolled slightly outward, but becoming loosely rolled outward later at maturity.
Petals:
*Appearance.*—Inside—satiny. Outside—velvety.
*Shape.*—Outer—oval, with apex mucronate. Intermediate—oval, with apex mucronate. Inner—obovate, with apex mucronate.

This description of a newly opened flower was made from a rose grown in a greenhouse during the month of October at Richmond, Ind.:

*Color.*—Outer petal: outside surface—slightly darker than Mandarin Red, Plate 17/2 (W), with base Naples Yellow, Plate 403/3 (W); inside surface—Mandarin Red, Plate 17 (W), with base Naples Yellow, Plate 403/3 (W). Intermediate petal—outside surface—slightly lighter than Mandarin Red, Plate 17/1 (W), with base Naples Yellow, Plate 403/3 (W); inside surface—Mandarin Red, Plate 17 (W), with base Naples Yellow, Plate 403/2 (W). Inner petal: outside surface—slightly lighter than Mandarin Red, Plate 17/1 (W), with base Naples Yellow, Plate 403/3 (W); inside surface—Mandarin Red, Plate 17 (W), with base Naples Yellow, Plate 403/1 (W).

This description was made from a rose that was open for three days in a greenhouse during the month of October at Richmond, Ind.:

*Color.*—Outer petal: outside surface—Scarlet, Plate 19/2 (W), with base Naples Yellow, Plate 403/3 (W); inside surface—Scarlet, Plate 19/1 (W), with base Naples Yellow, Plate 403/3(W). Intermediate petal: outside surface—Scarlet, Plate 19/2 (W), with base Naples Yellow, Plate 403/3 (W); inside surface—Scarlet, Plate 19/1 (W), with base Naples Yellow, Plate 403/3 (W). Inner petal: outside surface—Scarlet, Plate 19/2 (W), with base Naples Yellow, Plate 403/3 (W); inside surface—Scarlet, Plate 19/1 (W), with base Naples Yellow, Plate 403/3 (W).

*General color effect.*— Newly opened flower—Scarlet, Plate 19 (W). 3-days open—Scarlet, Plate 19 (W).

*Behavior (in greenhouse).*—Petals persist; affected by extremely hot weather by a slight decrease in petal size; and fading to Scarlet, Plate 19/1 (W).

*Flower longevity.*—Cut roses in greenhouse and kept at living room temperatures—7 days in October.

*Plant*

Foliage:

*Leaves.*—Compound of usually 5 to 7 leaflets; normal abundance; medium size; thin; leathery.

*Leaflets.* — Shape — elliptical. Apex — cuspidate. Base—obtuse. Margin—serrate.

*Color.*—Mature: upper surface—Ivy Green, Plate 0001060/2 (W); under surface—slightly lighter than Spinach Green. Plate 0960/3 (W). Young: upper surface—Parsley Green, Plate 00962 (W); under surface—slightly lighter than Spinach Green, Plate 0960/3 (W).

*Rachis (the supporting stem of the compound leaf).*—Medium size. Upper side—grooved; hairy. Under side—prickly.

*Stipules.*—Moderately short; narrow; with short points turning out at an angle of more than 45°; recurved toward the stem.

Growth (in greenhouse):

*Habit.*—Bush; upright; much-branched.

*Growth.*—Free; vigorous.

*Canes.*—Small.

*Main stems.*—Color—Parsley Green, Plate 00962/3 (W). Thorns—several; medium length; from straight to slightly hooked downward; with short and narrow base; color—Garnet Brown, Plate 00918/3 (W). Prickles—several; color—Mimosa Yellow, Plate 602/3 (W), with darker tip. Hairs—none.

*Branches.*—Color—Parsley Green, Plate 00962/3 (W). Thorns—very few; medium length; from straight to slightly hooked downward; with narrow base; color—Garnet Brown, Plate 00918/3 (W). Prickles—very few; color—Mimosa Yellow, Plate 602/3 (W), with darker tip. Hairs—none.

*New shoots.*—Color—slightly lighter than Garnet Brown, Plate 00918/3 (W). Thorns—several; short; from straight to hooked slightly downward; with short base; color—Oxblood Red, Plate 00823/3 (W). Prickles—none. Hairs—none.

*Reproductive organs*

Stamens: Medium number; arranged regularly about pistils; tucked in calyx:

Filaments: Medium length; most with anthers. Color—Primrose Yellow, Plate 601/3 (W).

Anthers: Small; open at various times. Color—Orange buff, Plate 507 (W).

Pollen: Moderate quantity. Color—Orpiment Orange, Plate 10/2 (W).

Styles: Uneven; short; moderately thin; loosely bunched. Color—Primrose Yellow, Plate 601/3 (W).

Pistils: Medium number.

Stigma: Color—Sap Green, Plate 62/3 (W).

Ovaries: All encased in calyx.

Hips: Medium length; ovoid; with inconspicuous neck; gourd shaped; moderately smooth; walls thin and dry. Color—none observed.

Sepals: Permanent; medium length; spear shaped. Color: inside—Apple Green, Plate #77 (K); outside—slightly darker than Cedar Green, Plate #88 (K).

Seeds: Few; small.

I claim:

1. A new and distinct variety of rose plant of the floribunda class, substantially as herein shown and described, characterized particularly as to novelty by the unique combination of an upright habit of growth, uniformity of cane size, excellent flower productivity when grown under glass, a distinctive and attractive salmon-orange flower color and excellent keeping qualities of the flowers as cut flowers.

No references cited.

ROBERT E. BAGWELL, *Primary Examiner.*